United States Patent [19]

Hiltebrandt et al.

[11] 4,031,898

[45] June 28, 1977

[54] SURGICAL INSTRUMENT FOR COAGULATION PURPOSES

[76] Inventors: Siegfried Hiltebrandt, Aug.-Lammle-Str. 16, D-7134 Knittlelingen; Helmut Wurster, Mozartstr. 20, D-7519 Oberderdingen, both of Germany

[22] Filed: Sept. 13, 1976

[21] Appl. No.: 722,926

Related U.S. Application Data

[63] Continuation of Ser. No. 529,042, Dec. 3, 1974, abandoned.

[52] U.S. Cl. .............................................. 128/303.1
[51] Int. Cl.² ..................... A61N 3/04; A61B 17/38
[58] Field of Search ..................... 128/303.1, 303.17

[56] References Cited
UNITED STATES PATENTS

| 3,315,678 | 4/1967 | Donelson | 128/303.18 |
| 3,338,233 | 8/1967 | Grosholz et al. | 128/1 |
| 3,768,482 | 10/1973 | Shaw | 128/303.1 |
| 3,789,853 | 2/1974 | Reinhard | 128/399 |
| 3,801,800 | 4/1974 | Newton | 128/303.17 X |
| 3,826,263 | 7/1974 | Cage et al. | 128/303.1 |
| 3,929,137 | 12/1975 | Gonser | 128/303.14 |

*Primary Examiner*—Channing L. Pace

[57] ABSTRACT

This invention relates to surgical instruments such as probes or forceps which are heated from an external current source, and more particularly to such instruments which are used, for example, for laparoscopy.

The invention consists in the provision of a switch in the circuit of a heating element, a settable electronic control means for closing said switch for an adjustable length of time and means for automatically opening said switch for a length of time equivalent to the cooling-off period for the appropriate part of said instrument.

1 Claim, 6 Drawing Figures

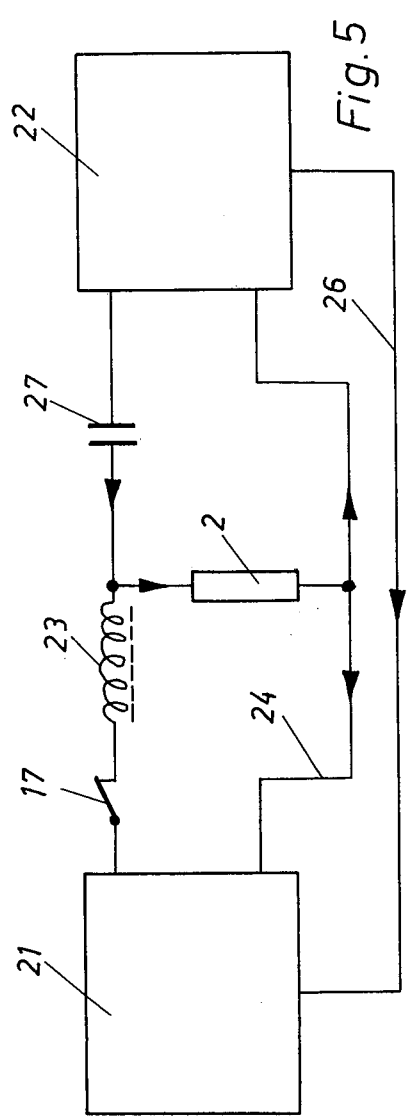
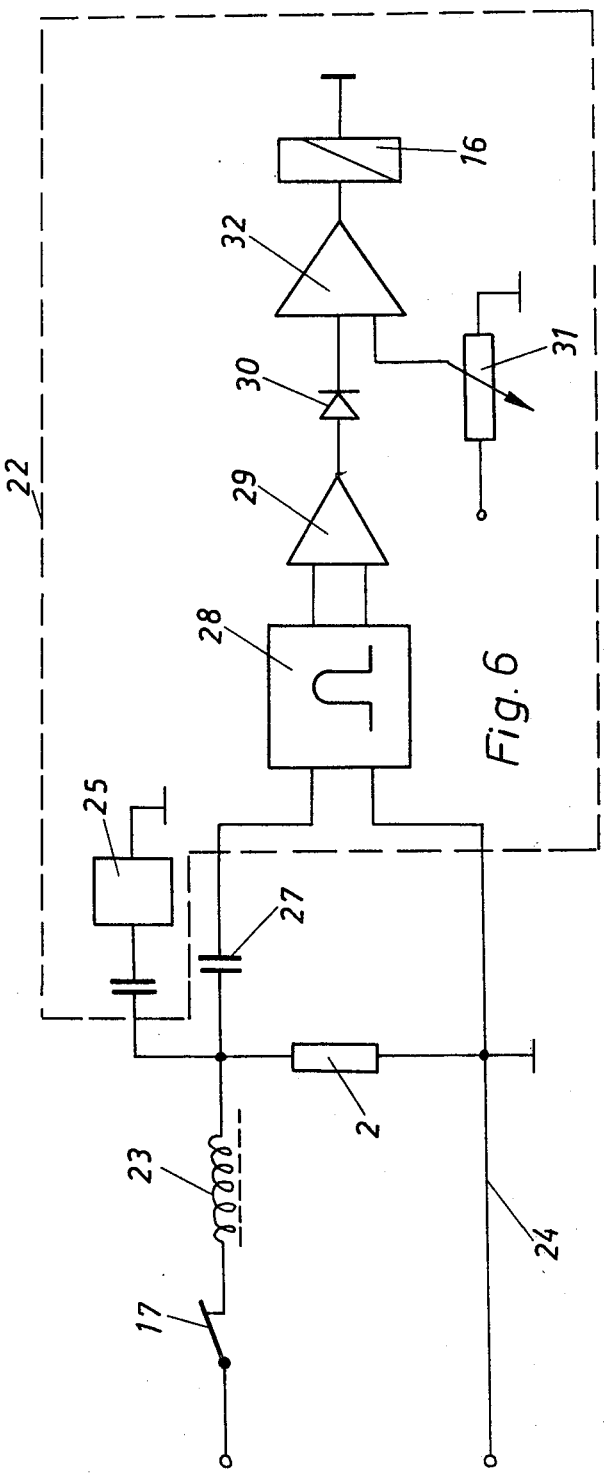
Fig.5
Fig.6

4,031,898

SURGICAL INSTRUMENT FOR COAGULATION PURPOSES

This is a continuation of application Ser. No. 529,042, filed Dec. 3, 1974, now abandoned. BACKGROUND OF THE INVENTION The present invention relates to coagulation probes or coagulation forceps for endoscopes, and especially hysteroscopes, having a plastics-coated head or jaws in which is housed an electrical heating element which is connectable to an electrical current supply source. Hereinafter, such a probe or forceps will be referred to as "a surgical instrument of the kind described".

To prevent uncontrollable HF currents from existing when areas of tissue are being coagulated, in human body-cavities, particularly in hysteroscopy, the practice has been adopted in recent times of using coagulation temperatures of approximately 110° to 150°. This was achieved by mounting heating elements in the heads of probes or the jaws of forceps, for the purpose of inactivating thermolabile tissue. In this way the danger of current being transmitted into the tissue, especially in the case of hysteroscopy in the ostia of the fallopian tubes or in gynaecological laparoscopy (e.g. for sterilising or temporarily sterilising women) was removed.

While a coagulation is being performed it has hitherto been necessary for the doctor to switch on the heating current and then switch it off again after the coagulation period, and then observe a cooling-off period for the probe-head or the jaws of the forceps before the probe or forceps can be removed. These operations hamper the activities of the doctor while he is observing the coagulation process.

Therefore, it is an object of the invention to provide a probe or forceps which relieves the doctor of the need to switch off the instrument eventually and of the need to observe waiting times during tissue coagulation, while at the same time keeping the coagulation period and the cooling down period for the probe or forceps under automatic supervision.

SUMMARY OF THE INVENTION

This object is achieved in accordance with the invention by providing a switch in a surgical instrument of the kind described said switch being in the circuit to the heating element which is closed by a settable electronic control means for an adjustable length of time, and which then opens automatically for a length of time equivalent to the cooling-off period for the appropriate part of said instrument. In a probe, such appropriate part is the head thereof, and in a forceps, the appropriate part is the jaws thereof.

At the same time it is advantageous for the heating and cooling off periods to be indicated by different signals so that the doctor will at all times be in a position to concentrate his entire attention on coagulating the area of tissue concerned while observing it endoscopically.

The automatic control means is so designed that the progress of its operation can at any time be interrupted to enable the heating period to be shortened by opening the switch or releasing a footswitch prematurely, or to enable the heating period to be prolonged once it has automatically come to an end by a fresh actuation, in which latter case the cooling-off period starts afresh when the heating means is switched off and the doctor can then open the forceps or remove the probe, as the case may be, when this period is at an end.

Since the radiation of heat from the heating element or the instrument needs to be as uniform as possible during the heating period, it is further proposed in accordance with the invention that the heating element in the automatically controlled circuit for heating current, which can be switched on and off, be used directly as a temperature sensor by having the resistance of the heating element, which is dependant on the temperature of the heating element at any particular time, act on a temperature monitoring means for re-adjusting the heating circuit. This makes it unnecessary for the physical size of the probe or forceps to be increased, for this would result in the diameter of the endoscope barrel being larger remembering that, inter alia, the usual endoscopic optical system, light conductor and possibly other components pass through this barrel in addition to the passage through which the probe or forceps is inserted. Since the heating element is incorporated directly into the monitoring means, this arrangement also allows any alteration in the temperature of the heating element to be detected directly and rapidly and used to re-adjust the heating circuit. This not only reduces sources of error in general but also shortens the response times of the regulating circuitry.

BRIEF DESCRIPTION OF THE DRAWINGS

In order that the invention may be more clearly understood, reference will now be made to the accompanying drawings which show some embodiments thereof by way of example and in which:

FIG. 5 shows a block diagram of the electrical temperature control means for a heating element, and FIG. 6 shows the circuit diagram of a temperature control circuit.

SPECIFIC DESCRIPTION OF PREFERRED EMBODIMENTS

Figure 1:
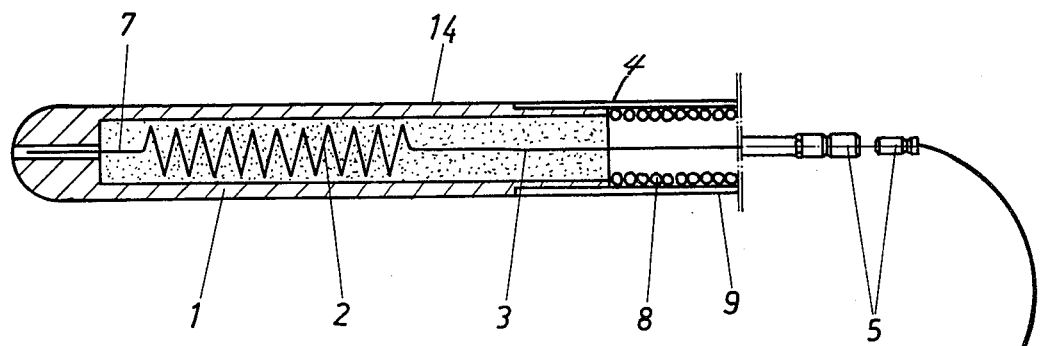
FIG. 1 shows a flexible coagulation probe, with an enlarged axial section through the head of the probe and a side-view of part of the probe.

Referring now to the drawings, the embodiment shown in FIG. 1 is a coagulation probe, having a metal head 1 which contains within it a heating element 2 (e.g. a heating coil) one end of which can be connected to one pole of a source of current supply via an insulated conductor 3 inside the flexible barrel 4, an electric plug-in connection 5, and a cable 6. The other end 7 of the heating coil 2 is soldered into the head 1 of the probe and has a path back to the current supply source through the flexible barrel 4 via a coil spring 8 contained in a yielding sleeve 9, and then through the connection 5 and the cable 6. The barrel may alternately also be rigid.

Figure 2:
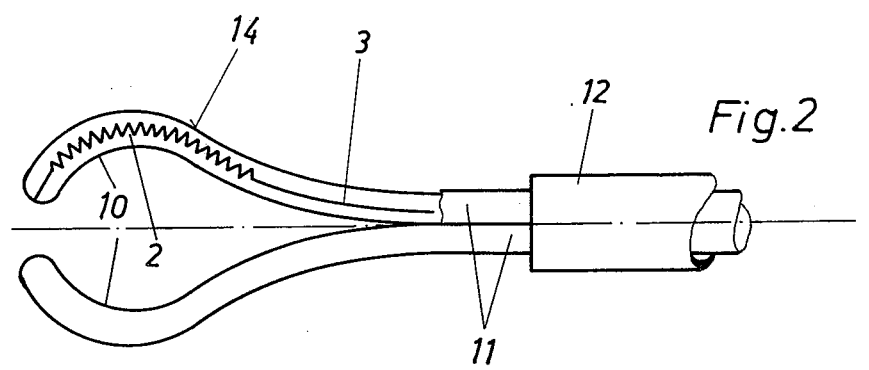
FIG. 2 shows an enlarged view of the jaws of a coagulation forceps with a longitudinal section through one of the arms which form the jaws.
Figure 3:
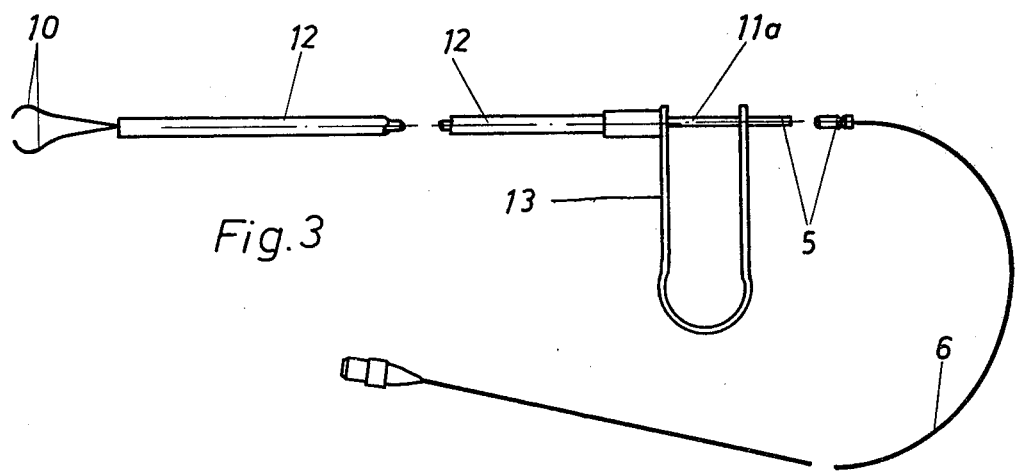
FIG. 3 shows schematic general view of the coagulation forceps.

When a coagulation forceps as shown in FIGS. 2 and 3 is used, e.g. for closing off a fallopian tube, heating coils 2 are housed in both of the jaws 10 of the forceps and these coils too are connectable to a current supply source via insulated conductors 3, the arms 11 of the forceps (which are joined to a tube 11a inside a rigid tubular barrel 12), an electrical plug-in connection 5 and the cable 6. The resilient arms 11 of the forceps, or their tubular extension 11a, extend through the barrel 12 and the proximal end of the barrel is connected to one side of a U-shaped resilient handle 13 the other side of which engages with the tube 11a carrying the jaws. The jaws 10 of the forceps can be opened or closed by operating the handle 13.

To prevent the areas of tissue from sticking to the probe-head 1 or the arms 10 of the forceps when they are heated up by the heating elements 2, the head 1 and the jaws 10 are provided with a thin coating 14 of a plastics material which prevents tissue from sticking but is nevertheless sufficiently thin to allow the requisite heat from the heated head 1 or jaws 10 to pass through it. This coating layer 14 should therefore be extremely thin and may be made such as to be imperceptible to the naked eye.

Figure 4:
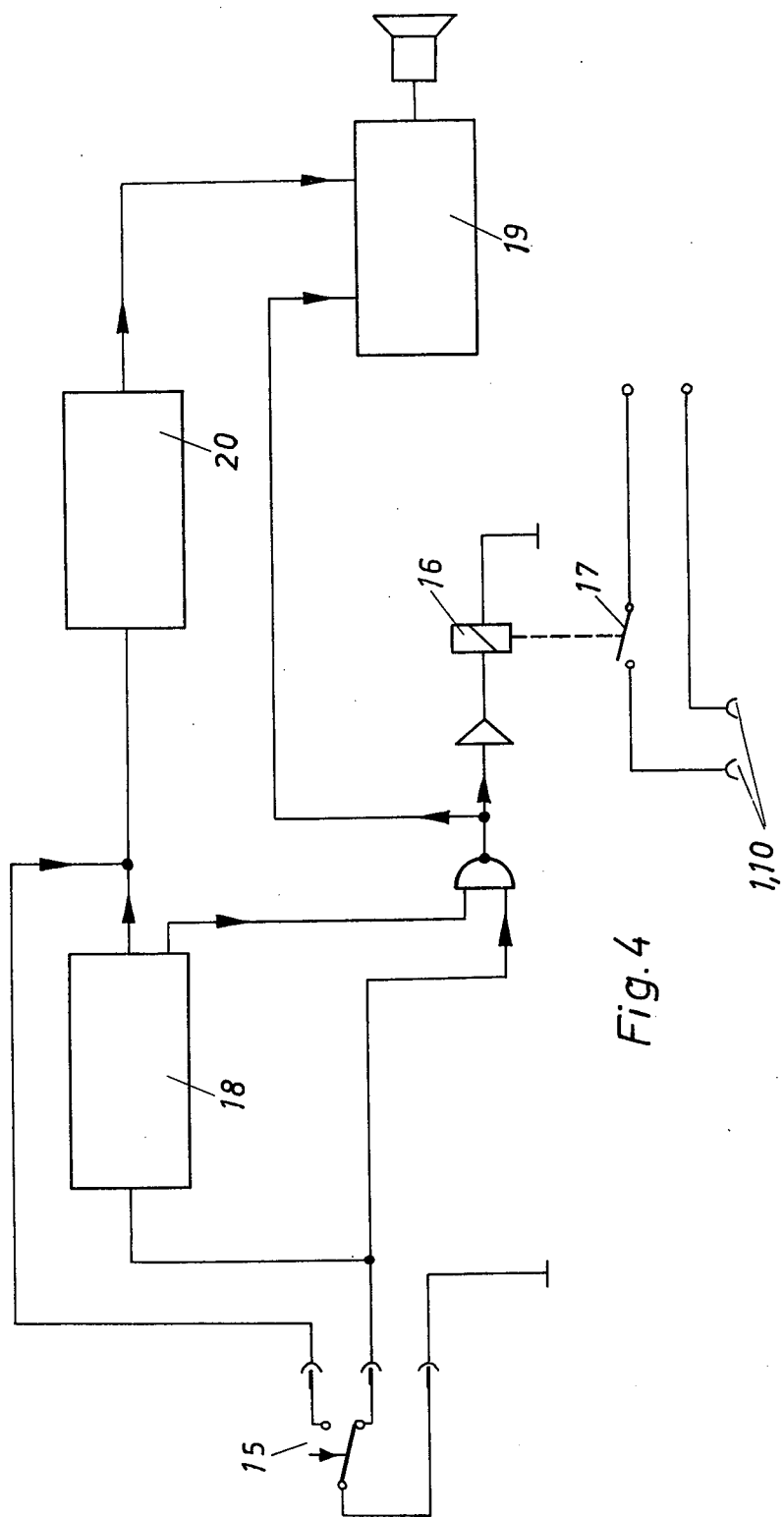
FIG. 4 shows a block diagram of the circuit of the control means for the coagulation probe of FIG. 1 or the coagulation forceps of FIGS. 2 and 3.

For probes or forceps (to be used efficiently) it is necessary on the one hand to relieve the doctor of incidental activities and on the other to be able to set a cooling-off period and a heating period (coagulation period) which can be adjusted to suit the type of instrument and the structure of the tissue to be coagulated. This is done by means of an electronic control device which is shown in FIG. 4. This device is switched on by means of a switch 15 (which is advantageously a foot-switch) and in this way a switch 17 in the circuit to the heating coil 2 of the probe or forceps is closed, via a relay 16. The probe head 1 or the jaws 10 of the forceps heat up until the requisite coagulation temperature, which is advantageously between 110° and 140° C, is reached. The total coagulation period (heating period) can be set by means of circuit 18 and when it begins a continuous, high-frequency sound is generated by a sound generator 19 which is actuated. This sound stops only when the heating period ends and the ending of the period also causes relay 16 to be acted upon so as to effect switch 17 in the circuit to de-energize the heating coil 2. At the end of the heating period begins the cooling-off period for the probe-head or forceps jaws. This period is indicated by the triggering of circuit 20 and it causes the sound generator to produce a different sound, e.g. a low sound, as a signal to the doctor. This sound ceases only when the cooling-off period is over. Using this control means it becomes possible to coagulate or inactivate areas of tissue entirely without risk while they are kept under endoscopic observation. It is understood that other signals, such as visual signals, could be used in place of different audible sounds.

In order automatically to hold the heat radiation from heating element 2, (i.e. the requisite coagulation temperature, which may be between approximately 110° and 140° C) constant during the heating period, the circuit shown in FIG. 4 is supplemented by that shown in FIG. 5.

In FIG. 5 the control device in FIG. 4 is represented by block 21, which also contains the DC supply for the heating element 2 in the probe or forceps. The heating element, or the probe or forceps, of FIGS. 1 to 3, is shown in FIG. 5 in the manner conventional for circuit diagrams as a resistor 2. The watch which needs to be kept on the probe temperature which has been set is carried out by a temperature control means which appears as block 22 in FIG. 5. The circuitry of this means is shown in detail in FIG. 6 in the block 22 which appears within a broken line. The temperature control means 22 gives control orders via line 26 to the circuit for heating current in control device 21 when the temperture found at the probe or forceps jaws at any particular time exceeds or otherwise deviates from the value it should have, at which time it is necessary to re-adjust or temporarily switch off the heating current.

During the heating up process the heating current from control device 21 flows through the closed contact 17 of control relay 16, through a choke 23, which acts as a barrier to alternating current, through heating element 2, and then along line 24 and back to the circuit for heating current in control device 21. In the probe, i.e. in the heating element 2, the DC heating current has superimposed on it an alternating current which is generated by a generator 25. When this is done choke 23 forms a barrier to AC between the temperature control means 22 and the heating current circuit.

Since the heating element itself is used, in accordance with the invention, as a temperature sensor, the level of alternating current through the heating element at any particular time gives an easy and direct indication of the heating temperature at this time. If at the same time a constant AC current produced by generator 25 is fed through the heating element, the temperature level in and the resistance of the heating element is in a direct linear relationship with the drop in AC voltage across the heating element 2 and this, once determined, is made use of to control the heating current.

The AC voltage existing in the heating element is fed, in the capacity of a measurement voltage, to a band-pass filter 28, via a coupling capacitor 27 which forms a barrier to DC between the circuit components for evaluating the measuring voltage and the heating circuit. The centre frequency of the band-pass filter is matched to the operating frequency of the AC generator 25, which may for example operate as a sound generator having a frequency of 5KHz. The filter is intended to ensure that unwanted voltages are filtered out and that only the 5KHz measurement voltage signal is evaluated. After first being amplified in an amplifier 29, the measurement voltage is rectified by a rectifier 30.

To detect deviations on the part of the coagulation temperature from a predetermined desired value, in this embodiment, the procedure is that a reference voltage, which is related to the desired temperature value and which is fixed by calibration, is tapped off in the form of a DC voltage from a terminal of potentiometer 31 and compared with the measurement voltage which exists at the time. This is done by means of a difference amplifier 32, to the two inputs of which are fed on the one hand the DC measurement voltage and on the other the DC reference voltage.

Assuming that the difference amplifier is symmetrically constructed, if it is suitably tuned and if two input voltages of equal magnitude are fed into it, the output signal will be zero. Relating this to the present instance, this would mean that the measurement voltage and the voltage equivalent to the desired value which had been set were of equal magnitude and that no re-adjustment of temperature was necessary. If on the other hand the measurement voltage should rise, due to an increse in temperature in the heating element 2 and the increase in its resistance which this involves (which presupposes a heating element which has a positive temperature co-efficient), a voltage would arise at the output of the difference amplifier.

This voltage can be used to act on the relay 16 and thus operate its associated switch 17, so as to interrupt the heating current, for as long as a voltage exists at the output of the difference amplifier. Once the heating element has cooled down to the desired temperature level or to a working temperature somewhat below this desired value, relay 16 will react appropriately, as there will be no difference voltage at the output of amplifier 32 under these circumstances. When the relay reacts, contact 17 closes so as to switch the line for the heating current back through to the heating element. It will be appreciated that the regulating circuit, which in principle operates cyclically, may be so designed that it is possible to control temperature within fine and accurate limits about the desired value. Instead of a heating element having ohmic resistance and a positive temperature co-efficient it would also be possible to use heating elements such as Negative temperature coefficient semiconductors, which have a negative temperature co-efficient, and which would call for only slight and well-known steps to be taken to modify the circuitry and polarities. Further, it is of course possible to replace the difference amplifier and the associated regulating potentiometer by a Schmitt trigger whose reference value can be altered. Finally it would be possible, in place of control relay 16, to use an adjustable amplifier which is governed by a current setter similar to the resistance of the heating element.

We claim:

1. A coagulation probe having a head and having a heating element embodied within the head, the head being adapted to be heated up to a predetermined maximum temperature in a temperature range extending from about 110° C to about 150° C necessary for the coagulation of thermolabile tissue during a predetermined heating period and alternating cooling-off period for the head, the heating element being a part of a circuit energized by electrical current of an electrical voltage source and being adapted to be switched-off initiating and during the cooling-off period such that after this later period a sticking of tissue to the head is prevented, the said circuit having switch means for opening and closing said circuit adapted thereby to energize and deenergize respectively, the heating element, said switch means adapted to be automatically controlled by a settable electronic control means for closing said switch for a predetermined adjustable length of time and opening said switch for a predetermined length of time substantially equivalent to said cooling-off period and for working signal means giving signals at respectively a beginning and an end of said heating period, and giving a different signal for indicating the end of the cooling-off period.

* * * * *